(12) United States Patent
Li et al.

(10) Patent No.: US 9,290,435 B2
(45) Date of Patent: Mar. 22, 2016

(54) MOLECULAR GLASS OF SPIROFLUORENE DERIVATIVE, PREPARATION METHOD THEREOF AND USE THEREOF IN PHOTO-ETCHING

(71) Applicant: Technical Institute of Physics and Chemistry of the Chinese Academy of Sciences, Beijing (CN)

(72) Inventors: Yi Li, Beijing (CN); Qingshan Hao, Beijing (CN); Jinping Chen, Beijing (CN); Yi Zeng, Beijing (CN); Tianjun Yu, Beijing (CN)

(73) Assignee: Technical Institute of Physics and Chemistry of the Chinese Academy of Sciences, Beijing (CN)

( * ) Notice: Subject to any disclaimer, the term of this patent is extended or adjusted under 35 U.S.C. 154(b) by 0 days.

(21) Appl. No.: 14/762,260

(22) PCT Filed: Jan. 22, 2013

(86) PCT No.: PCT/CN2013/070825
§ 371 (c)(1),
(2) Date: Jul. 21, 2015

(87) PCT Pub. No.: WO2014/113914
PCT Pub. Date: Jul. 31, 2014

(65) Prior Publication Data
US 2015/0353468 A1 Dec. 10, 2015

(51) Int. Cl.
*C07C 37/055* (2006.01)
*G03F 7/004* (2006.01)
*C07C 69/708* (2006.01)
*C07C 43/205* (2006.01)
*C07C 39/23* (2006.01)
*C07C 67/00* (2006.01)
*C07C 69/96* (2006.01)
*C07C 41/30* (2006.01)

(52) U.S. Cl.
CPC ............ *C07C 69/708* (2013.01); *C07C 37/055* (2013.01); *C07C 39/23* (2013.01); *C07C 41/30* (2013.01); *C07C 43/2055* (2013.01); *C07C 67/00* (2013.01); *C07C 69/96* (2013.01); *G03F 7/004* (2013.01); *G03F 7/0045* (2013.01); *C07C 2103/94* (2013.01)

(58) Field of Classification Search
CPC .. C07C 37/055; C07C 41/30; C07C 43/2055; C07C 39/17; C07C 39/23; C07C 69/708; C07C 69/96; G03F 7/004; G03F 7/0045
USPC .................. 430/270.1, 913, 927; 560/76, 96; 568/633, 719
See application file for complete search history.

(56) References Cited

U.S. PATENT DOCUMENTS

| | | | | |
|---|---|---|---|---|
| 6,187,224 | B1 * | 2/2001 | Kreuder | C07C 255/51 252/301.21 |
| 2005/0164034 | A1 * | 7/2005 | Park | C09K 11/06 428/690 |
| 2008/0044757 | A1 | 2/2008 | De Silva et al. | |
| 2010/0244693 | A1 * | 9/2010 | Kawakami | C07C 211/61 315/32 |
| 2010/0277061 | A1 * | 11/2010 | Matsuura | C07C 13/567 313/504 |
| 2011/0147728 | A1 * | 6/2011 | Kawakami | C07C 211/61 257/40 |
| 2011/0260114 | A1 | 10/2011 | Wu et al. | |

FOREIGN PATENT DOCUMENTS

CN 102557930 7/2012

OTHER PUBLICATIONS

Chu et al, "Synthesis of Dendritic Oligo-Spiro(fluorene-9,9'-xanthene) Derivatives with Carbazole and Fluorene Pendants and their Thermal, Optical, and Electroluminescent Properties",Macromolecular Rapid Communication vol. 30, 1745-1750. (2009).*
Cha et al, "New sprio[benzotetraphene-fluorene] Derivatives: Synthesis and Application in Sky-Blue Fluorescent Host Materials", Journal of Fluorescence, vol. 24, Issue 4, pp. 1215-1224. (2014).*
Yu et al, "Fluorene-Based Light-Emitting Polymers", Chinese Journal of Polymer Science, vol. 19, No. 6, 603-613. (2001).*
International Search Report of PCT/CN2013/070825 dated Oct. 31, 2013, 3 pages.
International Search Report of PCT/CN2013/070825 dated Oct. 31, 2013, 3 pages (English translation).
Article: Xu, C., et al.: "Compact Hybrid Cell Based on a Convoluted Nanowire Structure for Harvesting Solar and Mechanical Energy", Adv. Mater. vol. 23, No. 7, pp. 873-877, published Jan. 7, 2011 (Abstract only).
Office Action of CN201380000139.X dated Mar. 31, 2015 4 pages (discussed in IDS Concise Explanation).
IDS Concise Explanation.

* cited by examiner

Primary Examiner — Amanda C Walke
(74) Attorney, Agent, or Firm — Rankin, Hill & Clark LLP

(57) ABSTRACT

Disclosed is a molecular glass of a spirofluorene derivative having a molecular structure as follows: formula (I),

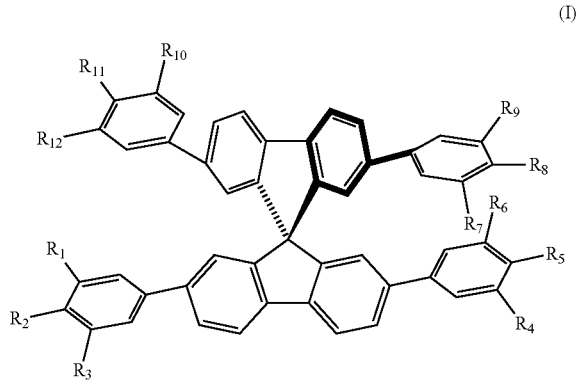

wherein each of $R_1$-$R_{12}$ is a hydrogen atom, a hydroxyl group, a methoxyl group or an acid-sensitive substituent; substituents $R_1$~$R_{12}$ can be identical or different, but on the same benzene ring the substituents cannot all be hydrogen atoms. The molecular glass has a good solubility in various polar solvents, is suitable to be made into a film; meanwhile the molecular glass has a very high glass transition temperature and meets the requirements of the photolithography processing technology. Also disclosed is a preparation method of the above-mentioned molecular glass of a spirofluorene derivative. The synthetic process of the method is simple and suitable for industrialization. Further disclosed is the use of a photo-resist with the above-mentioned molecular glass as a main material in photo-etching, wherein the molecular glass of a spirofluorene derivative with hydroxyl groups (or partly with hydroxyl groups) on the periphery thereof can be used as a negative photo-resist, and the molecular glass with the hydroxyl groups on the periphery thereof protected (or partly protected) by an acid-sensitive substituent can be used as a positive photo-resist.

19 Claims, 2 Drawing Sheets

MOLECULAR GLASS OF SPIROFLUORENE DERIVATIVE, PREPARATION METHOD THEREOF AND USE THEREOF IN PHOTO-ETCHING

FIELD OF THE INVENTION

The present invention belongs to the field of a material technology, particularly relates to a method for preparing a spirofluorene derivative molecular glass with a high glass transition temperature and a very good film-forming property and the use thereof as a main material of a photoresist in photolithography, especially in the extreme ultraviolet lithography.

BACKGROUND OF THE INVENTION

Photoresist (also known as photo-resist) refers to an etching resist film material whose solubility will change when it is irradiated or radiated by a light source such as a ultraviolet light, an excimer laser, electron beam, ion beam and x-rays. Photoresist is mainly used in microfabrication of integrated circuits and semiconductor discrete devices and finds a wide range of applications in manufacturing panel displays, LEDs, magnetic heads and precision sensors. The photoresist may be applied onto semiconductors, conductors and insulators by means of its photochemical reaction, due to photochemical sensitivity of the photoresist, and the remained portion after exposure and development provides protection for the substrate. Then a required fine pattern may be transferred from the mask onto the substrate to be processed by etching with the etchant. Therefore, the photoresist is a key material for the microfabrication technology. With improvements of technical requirements for integrated circuits, the resolution of a photolithography technology needs to be improved accordingly, from the early G-line (436 nm) photolithography, I-line (365 nm) photolithography, deep UV (248 nm) photolithography to the current 193 nm photolithography and further to the most promising next generation extreme ultraviolet (EUV, 13.5 nm) photolithography, and the photolithography technology accordingly put greater demands on the photoresist.

The main material of existing photoresist used in the 193 nm photolithography usually employs a low molecular weight polymer with the molecular weight of 5,000-15,000 Daltons. Such polymeric material may affect the edge roughness or line width roughness of the pattern generally due to the factors such as too large molecular volume, dispersive molecular weight and molecular chains' intertwinement, so that such polymeric material does not meet the demand of a fine photolithography. Therefore, it is very important to develop a novel photoresist for the photolithography technology.

Molecular glass is a kind of small molecule compound having specific structures and functions, which is proposed and developed in recent years. Such small molecule compound has an exact molecular structure, monodispersity and a small radius of gyration, meanwhile possesses thermal stability and film-forming property of a polymer, therefore it is expected to become a new kind of photoresist main material (Adv. Mater. 2008, 20, 3355). At present, the molecular glass developed as a photoresist main material is mainly a branched or cyclic structure compound with photosensitivity (or acid-sensitivity), wherein the branched structure is mainly a rigid structure with multi-benzene ring connection (J. Mater. Chem. 2008, 18, 1903; Chem Mater. 2008, 20, 1606), and the cyclic structure is mainly a calixarene or calixarene-like structure (J. Mater. Chem. 2008, 18, 3588; J. Mater. Chem. 2010, 20, 4445). In addition to photosensitivity (or acid-sensitivity), the glass transition temperature (Tg) and the film-forming property are two most important indicators to determine whether the molecular glass has applicability, when the molecular glass is designed and synthesized. If the synthetic compound is easy to crystallize or the glass transition temperature (Tg) is lower than 100° C., the glass transition temperature (Tg) and the film-forming property will directly affect the application of the molecular glass as a photoresist main material.

Spirofluorene structure has a geometric skeleton with two planes thereof being perpendicular to each other, which can effectively suppress inter-molecules crystallization and can be easy to form a film, meanwhile the spirofluorene has a good rigid structure, a high glass transition temperature and a good thermal stability. It will contribute to the improvements of the glass transition temperature and the film-forming property to design and synthesize a molecular glass based on the spirofluorene structure.

SUMMARY OF THE INVENTION

The first technical problem to be solved by the present invention is to provide a spirofluorene derivative molecular glass. The molecular glass has good solubility in various polar solvents which may lead to formation of a good film through a spin coating method, meanwhile it has a very high glass transition temperature (>100° C.) which may meet the requirements of a photolithography process.

The second technical problem to be solved by the present invention is to provide a method for preparing the above-mentioned spirofluorene derivative molecular glass. The method uses tetrabromo spirofluorene as a raw material, and a series of molecular glasses based on spirofluorene can be obtained through a simple coupling reaction, a deprotection reaction and functionalization modification. The synthetic process is simple, and the product can be isolated from a reaction system by recrystallization or precipitation.

The third technical problem to be solved by the present invention is to provide an application of a photoresist using the above-mentioned molecular glass as a main material in an extreme ultraviolet photolithography process.

In order to solve the above-mentioned first technical problem, the spirofluorene derivative molecular glass of the present invention has the following molecular structure:

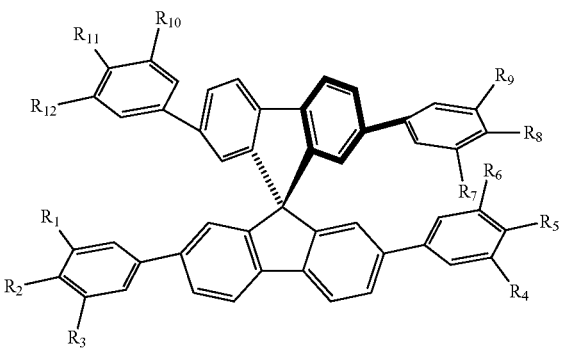

wherein:
the substituents $R_1$-$R_{12}$ are a hydrogen atom, a hydroxyl group, a methoxyl group or an acid-sensitive substituent, respectively; the substituents $R_1$-$R_{12}$ can be same or different, but the substituents on the same benzene ring cannot all be hydrogen atoms;

The acid-sensitive substituent is alkane carbonic ester with no more than 12 carbon atoms, and the structure thereof is:

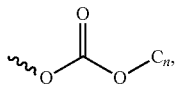

or alkane α-acetate substituent, and the structure thereof is:

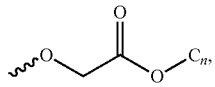

wherein $C_n = C_{1-12}$ alkyl, ⌇ represents a connecting bond.

Preferably, the alkane carbonic ester with no more than 12 carbon atoms or the alkane α-acetate substituent is a group with the following structure:

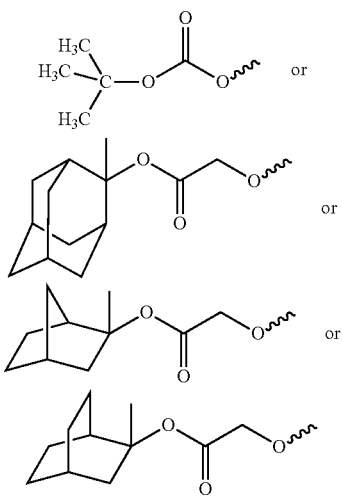

wherein, ⌇ represents a connecting bond.

In order to solve the above-mentioned second technical problem, the method for preparing spirofluorene derivative molecular glass of the present invention comprises the following steps of:

1) under the protection of an inert gas, mixing spirofluorene having tetrabromo substituents with phenyl boride having methoxy substituents with different numbers and at different sites by 1:4-8 molar ratio; adding palladium acetate as a catalyst with catalytic amount and a tetrahydrofuran solution; heating up to 50-70° C. and keeping reaction for 6-24 hours to obtain a spirofluorene derivative having different phenylmethoxy substituents;

2) under the protection of an inert gas, mixing the spirofluorene derivative obtained in step 1) with $BF_3$ by 1:8-10 molar ratio; producing a deprotection reaction in a dichloromethane solvent at $-50°$ C.-$80°$ C. to obtain a spirofluorene derivative with phenolic hydroxyl groups at the periphery thereof;

3) under the protection of an inert gas, mixing the spirofluorene derivative obtained in step 2) and a compound containing an acid-sensitive substituent by 1:4-18 molar ratio; adding pyridine or potassium carbonate as a catalyst; producing a reaction at room temperature for 10-24 hours to obtain a spirofluorene derivative molecular glass.

The phenyl boride having methoxy substituents with different numbers and at different sites is one or more selected from the group consisting of p-methoxyphenyl pinacol borane, m-methoxyphenyl pinacol borane, 3,4-dimethoxyphenyl pinacol borane, 3,5-dimethoxyphenyl pinacol borane and 3,4,5-trimethoxyphenyl pinacols borane.

The compound containing an acid-sensitive substituent has the following structure:

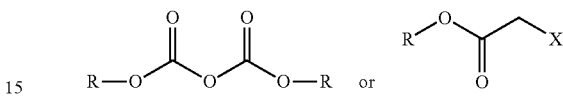

wherein, R represents an alkyl chain with no more than 12 carbon atoms; X=Cl, Br or I.

Preferably, the compound containing an acid-sensitive substituent has the following structure:

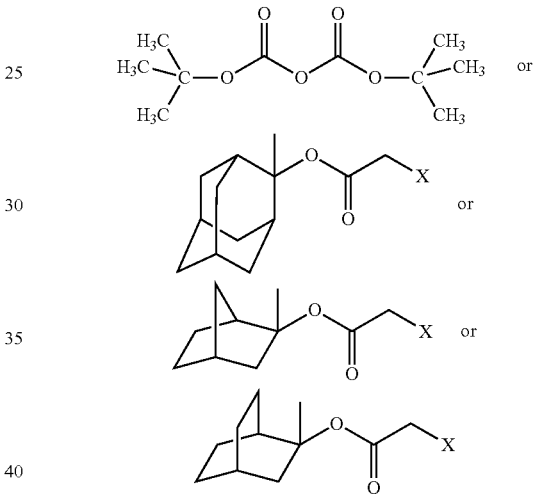

wherein, X=Cl, Br or I.

The present invention provides a use of a photoresist using the above-mentioned spirofluorene derivative molecular glass as a main material in photolithography. Wherein the spirofluorene derivative molecular glass with the peripheral substituents thereof being all or partially hydroxyl groups may be used as a negative photoresist. The spirofluorene derivative molecular glass with the peripheral substituents thereof being all or partially protected (i.e. substituted) by acid-sensitive substituents may be used as a positive photoresist.

The present invention further provides a negative photoresist formula, comprising the above-mentioned spirofluorene derivative molecular glass with the peripheral substituents thereof being all or partially hydroxyl groups used as a main material of the negative photoresist, a photo-acid-generating agent, a cross linking agent and a photoresist solvent. In the negative photoresist formula, at least four substituents $R_1$-$R_{12}$ of the spirofluorene derivative molecular glass may be hydroxyl groups. Preferably, the content of the spirofluorene derivative molecular glass main material is 1%-10% (by mass content), the content of the cross linking agent is 0.1 wt %-1 wt % (by mass content), the content of photo-acid-generating agent is 0.01 wt %-1 wt % (by mass content) and the remainder is the photoresist solvent.

The present invention further provides a positive photoresist formula, comprising the above-mentioned spirofluorene derivative molecular glass with the peripheral substituents thereof being all or partially acid-sensitive groups used as a main material of the positive photoresist, a photo-acid-generating agent, a cross linking agent and a photoresist solvent. In the positive photoresist formula, at least four substituents $R_1$-$R_{12}$ of the spirofluorene derivative molecular glass may be acid-sensitive substituents. Preferably, the content of the spirofluorene derivative molecular glass is 1 wt %-10 wt % (by mass content), the content of the photo-acid-generating agent is 0.01 wt %-1 wt % (by mass content) and the remainder is the photoresist solvent.

The photo-acid-generating agent may comprise an ionic photo-acid-generating agent and an non-ionic photo-acid-generating agent, such as triphenylsulfonium trifluoromethanesulfonate, bis(4-tert-butylphenyl)iodonium p-toluenesulfonate, N-hydroxynaphthalimide triflate, etc.; the cross linking agent comprises 1,3,4,6-tetrakis(methoxymethyl)glycoluril, 2,4-hydroxymethyl-6-methyl-phenol (2,4-DMMP), etc.; the photoresist solvent comprises propylene glycol monomethyl ether acetate (PGMEA), ethyl lactate, 2-methoxyethanol, cyclohexanone, etc.

The above mentioned positive or negative photoresist formula may further comprise other auxiliary additives, such as sensitizers, surfactants, anti-proliferation agents, stabilizers, etc.

The positive or negative photoresist formula of the present invention may be spin-coated onto a silicon wafer to form a film by a coating machine, so as to obtain a photoresist coating, and further the photolithography fringes with the resolution of less than 50 nm may be formed through interference photolithography.

Compared to the prior art, the present invention has the following advantages:

The synthetic process of a spirofluorene structure compound is simple, and the separation of a finished product from the reaction system can be realized by recrystallization or precipitation, which is suitable for industrialization. The characteristic of the geometry of the spirofluorene structure with two planes thereof being perpendicular to each other may contribute to suppression of the molecule crystallization and formation of a film; meanwhile it may meet the requirements of a photolithography process to design and synthesize the molecular glass based on the spirofluorene structure by means of high glass transition temperature and good thermal stability of the spirofluorene. Due to introduction of a large number of phenolic hydroxyl group in the spirofluorene, on one hand the interaction of the intermolecular hydrogen bonds is improved so that such molecular glass may show good film-forming properties and high glass transition temperature, on the other hand the hydroxy may be modified with the acid-sensitive group in a controllable way so that such molecular glass may be used as a main material of a photoresist for photolithography; the photoresist formula of the present invention may be used in modern lithographic process such as 248 nm photolithography, 193 nm photolithography, extreme ultraviolet (EUV) photolithography, nanoimprint lithography (NIL) and electron beam lithography (EBL), and particularly satisfy high-resolution requirements for photolithography fringes in the extreme ultraviolet (EUV) lithographic process.

BRIEF DESCRIPTION OF THE DRAWINGS

The embodiments of the present invention are further illustrated below with reference to drawings.

BRIEF DESCRIPTION OF THE PREFERRED EMBODIMENTS

Figure 1:
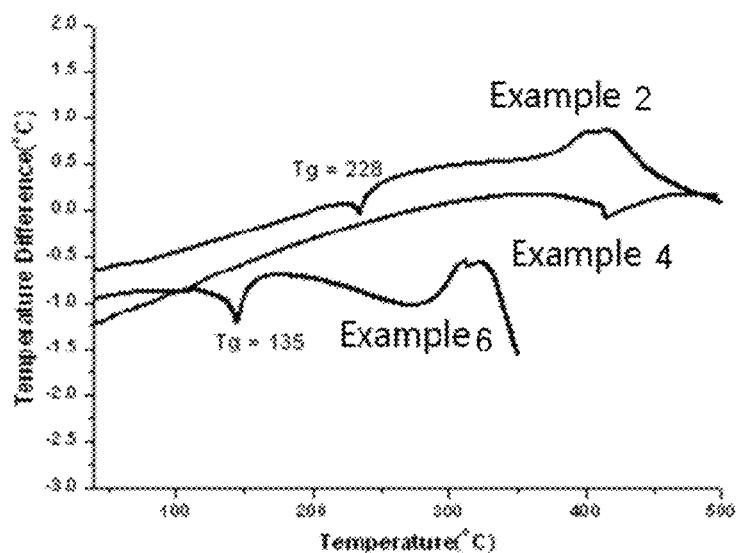
FIG. 1 shows a differential scanning thermal graph.

The present invention will be further illustrated below with reference to the embodiments for purpose of better understanding of the present invention. However, the protection scope of the present invention should include the entire contents of the claims, and is not limited thereto.

The present invention provides three methods for preparing phenyl boride with methoxy substituent for reference.

1. Preparing 3,5-dimethoxyphenyl boride, wherein the synthetic route is as follows:

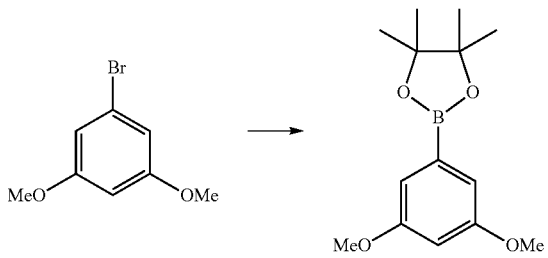 [SMILES: COc1cc(Br)cc(OC)c1 ; COc1cc(OC)cc(B2OC(C)(C)C(C)(C)O2)c1]

As follows are specific steps of: adding 3,5-dimethoxybromobenzene (1.74 g, 8.0 mmol, 1.0 equivalent (hereinafter referred to as 'eq')) and a catalyst $PdCl_2 (PPh_3)_2$ (281 mg, 0.4 mmol, 0.05 eq) into a 100 mL Schlenk reaction flask; performing a cycle of vacuumizing and filling nitrogen gas in the flask for three times; adding dried and redistilled 1,2-dichloroethane (20 ml), triethylamine (7 ml, 40 mmol, 5.0 eq) and pinacol borane (HBpin) (3.5 ml, 24.0 mmol, 3.0 eq) into the reaction flask by a syringe; heating the reaction system to 90° C. and performing a reflux reaction for 4 hours; cooling the reaction system down to room temperature, then pouring the reaction solution into 20 ml water to terminate the reaction; extracting aqueous phases with ethyl acetate for several times and combining organic phases; washing the organic phases with a saturated saline solution and water for one time, respectively; drying with anhydrous magnesium sulfate and spin-drying the solvent; recrystallizing an obtained product in n-hexane/ethyl acetate to obtain a 1.8 g white solid with the yield of 85%. $^1$H NMR (400 MHz, $CDCl_3$) δ (ppm) 7.03 (s, 2H, benzene), 6.90 (s, 1H, benzene), 3.84 (s, 6H, —OCH3), 1.33 (s, 12H, —CH3).

2. Preparing 3,4-dimethoxyphenyl boride, wherein the synthetic route is as follows:

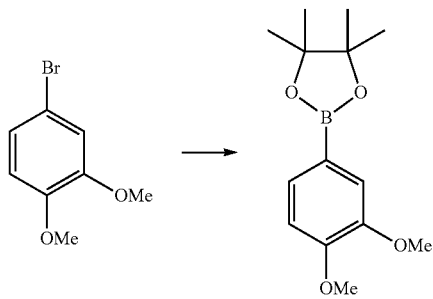 [SMILES: COc1ccc(Br)cc1OC ; COc1ccc(B2OC(C)(C)C(C)(C)O2)cc1OC]

As follows are specific steps of: adding 3,4-dimethoxy-bromobenzene (1.74 g, 8.0 mmol, 1.0 eq) and a catalyst PdCl$_2$(PPh$_3$)$_2$ (281 mg, 0.4 mmol, 0.05 eq) into a 100 ml Schlenk reaction flask; performing a cycle of vacuumizing and filling nitrogen gas in the flask for three times; adding dried and redistilled 1,2-dichloroethane (20 ml), triethylamine (7 ml, 40 mmol, 5.0 eq) and pinacol borane (HBpin) (3.5 ml, 24.0 mmol, 3.0 eq) into the reaction flask by a syringe; heating the reaction system to 90° C. and performing a reflux reaction for 4 hours; cooling the reaction system down to room temperature, then pouring the reaction solution into 20 ml water to terminate the reaction; extracting aqueous phase with ethyl acetate for several times and combining organic phases; washing the organic phases with a saturated saline solution and water for time, respectively; drying with anhydrous magnesium sulfate and spin-drying the solvent; recrystallizing an obtained product in n-hexane/ethyl acetate to obtain a 1.7 g white solid with the yield of 80%. $^1$H NMR (400 MHz, CDCl$_3$) δ (ppm) 7.15 (s, 1H, benzene), 7.05 (s, 1H, benzene), 6.90 (s, 1H, benzene), 3.84-3.86 (d, 6H, —OCH3), 1.32 (s, 12H, —CH3).

3. Preparing 3,4,5-trimethoxyphenyl boride, wherein the synthetic route is as follows:

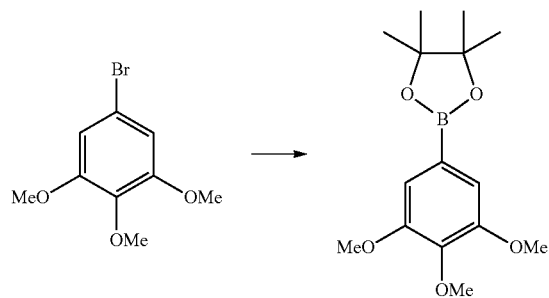 [SMILES: COc1cc(Br)cc(OC)c1OC ; COc1cc(B2OC(C)(C)C(C)(C)O2)cc(OC)c1OC]

As follows are specific steps of: adding 3,4,5-trimethoxy-bromobenzene (1.24 g, 5.0 mmol, 1.0 eq) and the catalyst PdCl$_2$ (PPh$_3$)$_2$ (176 mg, 0.25 mmol, 0.05 eq) into a 100 ml Schlenk reaction flask; performing a cycle of vacuumizing and filling nitrogen gas in the flask for three times; adding dried and redistilled 1,2-dichloroethane (15 ml), triethylamine (4.5 ml, 25 mmol, 5.0 eq) and HBpin (2.2 ml, 15.0 mmol, 3.0 eq) into the reaction flask by a syringe; heating the reaction system to 90° C. and performing a reflux reaction for 4 hours; cooling the reaction system down to room temperature, then pouring the reaction solution into 20 ml water; extracting aqueous phase with ethyl acetate for several times and combining organic phases; washing the organic phases with a saturated saline solution and water for one time, respectively; drying with anhydrous magnesium sulfate and spin-drying the solvent; recrystallizing an obtained product in n-hexane/ethyl acetate to obtain a 1.2 g white solid with the yield of 80%. $^1$H NMR (400 MHz, CDCl$_3$) δ (ppm) 7.03 (s, 2H, benzene), 3.90 (s, 6H, —OCH3), 3.87 (s, 3H, —OCH3), 1.34 (s, 12H, —CH3).

EXAMPLE 1

Preparing 2,7,2',7'-four-(3,5-dimethoxyphenyl)-9,9'-spirofluorene, wherein the synthetic route is as follows:

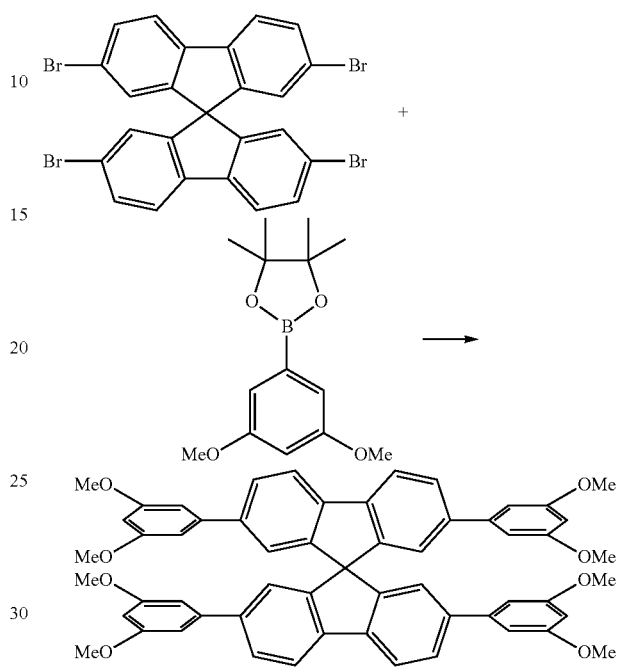

As follows are specific steps of: adding Pb(OAc)$_2$ (15.5 mg, 0.05 mmol, 0.1 eq), a ligand 2-dicyclohexyl-phosphorus-2',6'-dimethoxy-biphenyl-S-phos (49.8 mg, 0.1 mmol, 0.2 eq) into a 50 mL Schlenk reaction flask; performing a cycle of vacuumizing and filling nitrogen gas in the flask for three times; adding dried and redistilled tetrahydrofuran (5 mL) into the reaction flask by a syringe; stirring at room temperature for 30 minutes to obtain a catalyst solution and sealing the catalyst solution for use. The steps further comprise adding 2,7,2',7'-tetrabromo-spirofluorene (316.0 mg, 0.5 mmol, 1.0 eq) and 3,5-dimethoxyphenyl pinacol borane (660.0 mg, 2.5 mmol, 5.0 eq) into another 100 ml Schlenk reaction flask, performing a cycle of vacuumizing and filling nitrogen gas in the flask for three times; adding NaOH solution (1 ml, 5M), tetrahydrofuran (2 ml) and the above prepared catalyst solution by a syringe; heating the reaction solution to 60° C. for 6 hours; cooling the reaction solution down to room temperature; extracting aqueous phase with chloroform/water and combining organic layers; drying with anhydrous magnesium sulfate; removing the solvent by decompressing and condensing; recrystallizing the remainder with ether to obtain a 264 mg pale yellow solid with the yield of 61%. $^1$H NMR (400 MHz, CDCl$_3$) δ (ppm) 7.96 (d, J=7.9 Hz, 4H), 7.63 (d, J=8.0 Hz, 4H), 7.04 (s, 4H), 6.95 (s, 8H), 6.66 (s, 4H), 3.88 (s, 24H). MS (MALDI-TOF): m/z=860.8, calcd for (C$_{57}$H$_{48}$O$_8$) m/z=860.3 ([M]+).

EXAMPLE 2

Preparing 2,7,2',7'-four-(3,4,5-trimethoxyphenyl)-9,9'-spirofluorene, wherein the synthetic route is as follows:

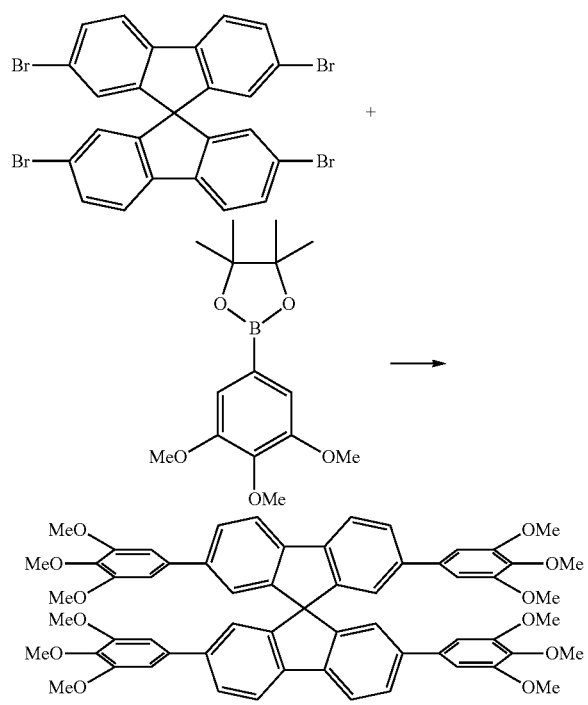

As follows are specific steps of: adding Pb(OAc)$_2$ (15.5 mg, 0.05 mmol, 0.1 eq), a ligand 2-dicyclohexyl-phosphorus-2',6'-dimethoxy-biphenyl-S-phos (49.8 mg, 0.1 mmol, 0.2 eq) into a 50 mL Schlenk reaction flask, performing a cycle of vacuumizing and filling nitrogen gas in the flask for three times; adding dried and redistilled tetrahydrofuran (5 mL) into the reaction flask by a syringe; stirring at room temperature for 30 minutes to obtain a catalyst solution and sealing the catalyst solution for use. The steps further comprise adding 2,7,2',7'-tetrabromo-spirofluorene (316.0 mg, 0.5 mmol, 1.0 eq) and 3,4,5-trimethoxyphenyl pinacol borane (735.0 mg, 2.5 mmol, 5.0 eq) into another 100 ml Schlenk reaction flask; performing a cycle of vacuumizing and filling nitrogen gas in the flask for three times; adding a NaOH solution (1 ml, 5M), tetrahydrofuran (2 ml) and the above prepared catalyst solution by a syringe; heating the reaction solution to 60° C. for 6 hours; cooling the reaction solution down to room temperature; extracting with chloroform/water and combining organic layers; drying with anhydrous magnesium sulfate; removing the solvent by decompressing and condensing; recrystallizing the remainder with ether to obtain a 319 mg pale yellow solid with the yield of 65%. $^1$H NMR (400 MHz, CDCl$_3$) δ (ppm) 7.94 (d, J=8.0 Hz, 4H), 7.61 (dd, J=8.0, 4H), 6.94 (d, J=1.2 Hz, 4H), 6.63 (s, 8H), 3.83 (d, J=8.1 Hz, 36H). MS (MALDI-TOF): m/z=980.3, calcd for C$_m$H$_{56}$O$_{12}$ m/z=980.1 ([M]+).

EXAMPLE 3

Preparing 2,7,2',7'-four-(3,5-dihydroxyl phenyl)-9,9'-spirofluorene, wherein the synthetic route is as follows:

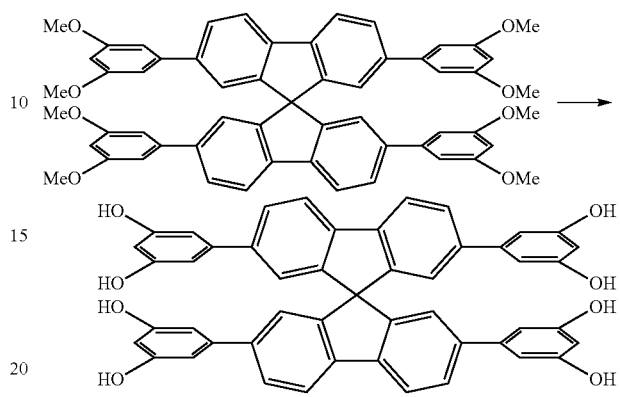

As follows are specific steps of: adding 2,7,2',7'-four-(3,5-dimethoxyphenyl)-9,9'-spirofluorene (1.0 g, 1.16 mmol, 1.0 eq) and 50 ml dichloromethane into a 250 ml three-necked flask; dissolving the same in nitrogen atmosphere; instilling a methylene chloride solution of boron tribromide (1M, 10 ml, 9.0 eq) into the reaction solution by a syringe at −78° C. to produce a reaction for 1 hour; heating the reaction solution up to room temperature gradually and keeping the reaction at the room temperature for 12 hours; adding 10 ml water slowly into the reaction solution to quench the reaction; removing dichloromethane solvent by decompressing; filtering the remainder to obtain a pale yellow filter cake; washing the filter cake with water and dichloromethane, respectively, so as to obtain a solid; precipitating the obtained solid with methanol/water for three times to obtain a 826 mg pale yellow solid with the yield of 95%. $^1$H NMR (400 MHz, DMSO-d$_6$) δ (ppm) 7.96 (d, J=7.9 Hz, 4H), 7.63 (d, J=8.0 Hz, 4H), 7.04 (s, 4H), 6.95 (s, 8H), 6.66 (s, 4H). MS (MALDI-TOF): m/z=748.6, calcd for (C$_{57}$H$_{48}$O$_8$) m/z=748.2 ([M]+).

EXAMPLE 4

Preparing 2,7,2',7'-four-(3,4,5-triihydroxyl phenyl)-9,9'-spirofluorene, wherein the synthetic route is as follows:

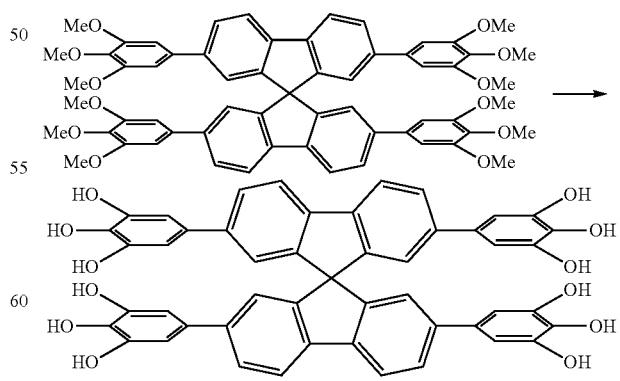

As follows are specific steps of: adding 2,7,2',7'-four-(3,4,5-triimethoxyphenyl)-9,9'-spirofluorene (981 mg, 1.0 mmol, 1.0 eq) and 50 ml dichloromethane into a 250 ml three-necked flask; dissolving the same in nitrogen atmosphere; instilling a dichloromethane solution of boron tribromide (1M, 18 ml, 18 eq) into the reaction solution by a syringe at −78° C. to produce a reaction for 1 hour; heating the reaction solution up to room temperature gradually and keeping the reaction at the room temperature for 12 hours; adding 10 ml water slowly into the reaction solution to quench the reaction; removing dichloromethane solvent by decompressing; filtering the remainder to obtain a pale yellow filter cake; washing the filter cake with water and dichloromethane, respectively, so as to obtain a solid; precipitating the obtained solid with methanol/water for three times to obtain a 756 mg pale yellow solid with the yield of 93%. $^1$H NMR (400 MHz, DMSO-d$_6$) δ (ppm) 8.05 (d, J=8.0 Hz, 4H), 7.58 (d, J=8.0 Hz, 4H, spirofluorene), 6.73 (s, 4H, spirofluorene), 6.39 (s, 8H, benzene) MS (MALDI-TOF): m/z=811.3, calcd for C$_{61}$H$_{56}$O$_{12}$ m/z=812.8 ([M]+).

EXAMPLE 5

Preparing 2,7,2',7'-four-(3,5-di-t-butyl carbonate phenyl)-9,9'-spirofluorene, wherein the synthetic route is as follows:

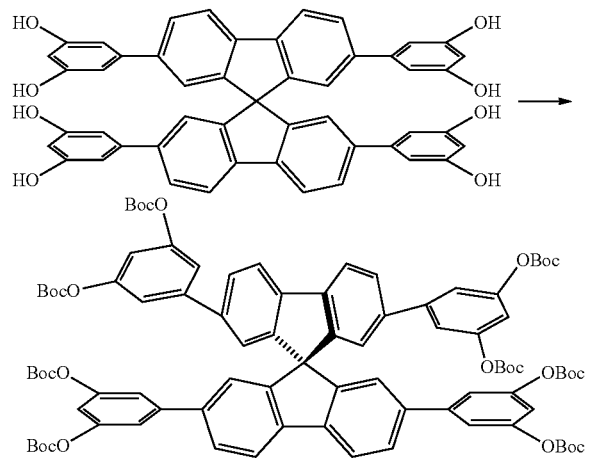

wherein Boc represents

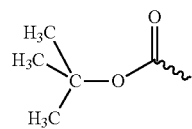

substituent.

As follows are specific steps of: adding 2,7,2',7'-four-(3,5-dihydroxyphenyl)-9,9' spirofluorene (500 mg, 0.67 mmol, 1.0 eq), tetrabutylammonium bromide (258 mg, 0.8 mmol, 1.2 eq) and pyridine (10 ml) into a 100 ml three-necked flask; stirring until the solid is dissolved; instilling Boc anhydride (di-tert-butyl dicarbonate ester) (2.34 g, 10.72 mmol, 16 eq) slowly into the reaction solution; heating the reaction solution up to 60° C. and keeping the reaction for 48 hours; cooling the reaction solution down to room temperature; extracting with dichloromethane/water; washing organic phases with citric acid aqueous solution for three times; drying the organic layers with anhydrous MgSO$_4$; removing the solvent by decompressing to obtain a semi-solid product; recrystallizing the semi-solid product in dichloromethane/n-hexane mixture to obtain a 883 mg white solid with the yield of 85%. $^1$H NMR (400 MHz, CDCl$_3$) δ (ppm) 7.83 (d, J=7.9 Hz, 4H), 7.52 (d, J=8.0 Hz, 4H), 6.98 (s, 4H), 6.81 (s, 8H), 6.44 (s, 4H), 0.81 (s, 72H), MS (MALDI-TOF): m/z=1549.0, calcd for C$_{89}$H$_{96}$O$_{24}$ m/z=1549.7 ([M]+).

EXAMPLE 6

Preparing 2,7,2',7'-four-(3,4-di-t-butyl carbonate phenyl)-9,9'-spirofluorene, wherein the synthetic route is as follows:

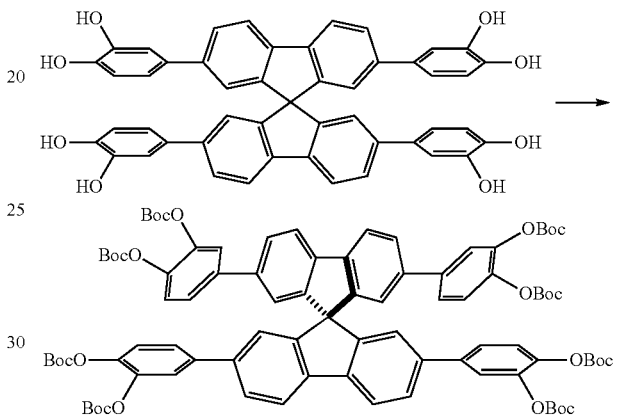

wherein Boc represents

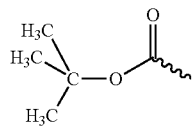

substituent.

As follows are specific steps of: adding 2,7,2',7'-four-(3,4-dihydroxyphenyl)-9,9'-spirofluorene (500 mg, 0.67 mmol, 1.0 eq), tetrabutylammonium bromide (258 mg, 0.8 mmol, 1.2 eq) and pyridine (10 ml) into a 100 ml three-necked flask; stirring until the solid is dissolved; instilling Boc anhydride (di-tert-butyl dicarbonate ester) (2.34 g, 10.72 mmol, 16 eq) slowly into the reaction solution; heating the reaction solution up to 60° C. and keeping the reaction for 48 hours; cooling the reaction solution down to room temperature; extracting with dichloromethane/water; washing organic phases with citric acid aqueous solution for three times; drying the organic layers with anhydrous MgSO$_4$; removing the solvent by decompressing to obtain a semi-solid product, recrystallizing the semi-solid product in dichloromethane/n-hexane mixture to obtain a 880 mg white solid with the yield of 85%. $^1$H NMR (400 MHz, CDCl$_3$) δ (ppm) 7.93-7.91 (d, 4H, spirobifluorene), 7.57-7.55 (d, 4H, spirobifluorene), 7.29 (s, 4H, spirobifluorene), 7.26-7.28 (d, 4H, Ar—H), 7.19-7.17 (d, 4H, Ar—H), 6.91 (s, 4H, Ar—H), 1.51 (m, 72H, t-Bu-H). MS (MALDI-TOF): m/z=1549.0, calcd for C$_{89}$H$_{96}$O$_{24}$ m/z=1549.7 ([M]+).

EXAMPLE 7

Preparing 2,7,2∝,7∝-four-(3-hydroxyl-5-t-butyl carbonate phenyl)-9,9'-spirofluorene, wherein the synthetic route is as follows:

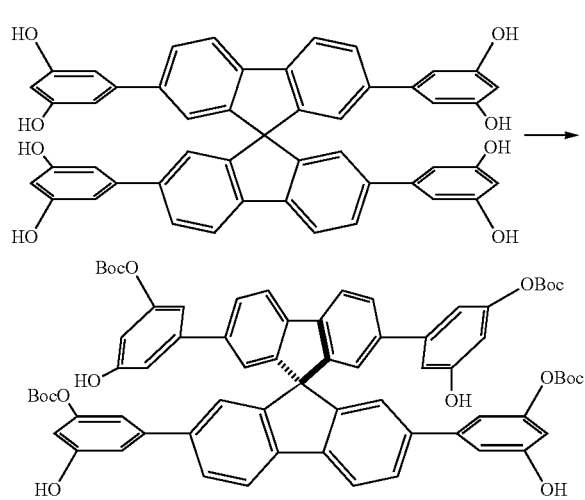

wherein Boc represents

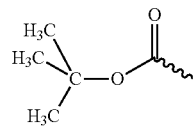

substituent.

As follows are specific steps of: adding 2,7,2',7'-four-(3,5-dihydroxyphenyl)-9,9'-spirofluorene (500 mg, 0.67 mmol, 1.0 eq), tetrabutylammonium bromide (258 mg, 0.8 mmol, 1.2 eq) and pyridine (10 ml) into a 100 ml three-necked flask; stirring until the solid is dissolved; instilling Boc anhydride (di-tert-butyl dicarbonate ester) (585 mg, 2.68 mmol, 4 eq) slowly into the reaction solution; heating the reaction solution up to 60° C. and keeping the reaction for 48 hours; cooling the reaction solution down to room temperature; extracting with dichloromethane/water; washing organic phases with citric acid aqueous solution for three times; drying the organic layers with anhydrous $MgSO_4$; removing the solvent by decompressing to obtain a pale yellow product; dissolving the pale yellow product into 10 ml dichloromethane to obtain a mixture and slowly instilling the mixture to 150 ml n-hexane to form a large of precipitates; filtering the precipitates for three times to obtain a 730 mg off-white solid with the yield of 95%. $^1$H NMR (400 MHz, $CDCl_3$) δ (ppm) 7.81 (d, J=7.9 Hz, 4H), 7.49 (d, J=8.0 Hz, 4H), 6.88 (s, 4H), 6.80 (s, 4H), 6.70 (s, 4H), 6.44 (s, 4H), 1.40 (s, 72H), MS (MALDI-TOF): m/z=1149.0, calcd for $C_{69}H_{64}O_{16}$ m/z=1148.4 ([M]+).

EXAMPLE 8

Preparing 2,7,2',7'-four-(3,4-dihydroxyl-5-acetate adamantyl phenyl)-9,9'-spirofluorene, wherein the synthetic route is as follows:

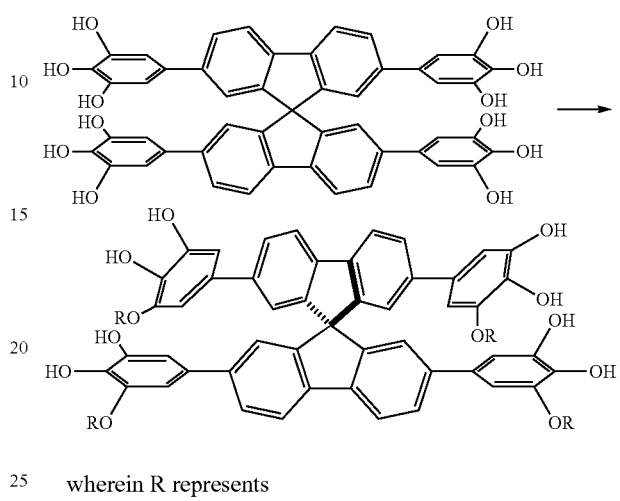

wherein R represents

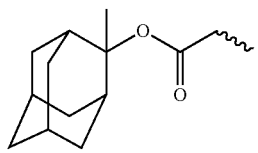

substituent.

As follows are specific steps of: adding 2,7,2',7'-four-(3,4,5-tridihydroxyphenyl)-9,9'-spirofluorene (406 mg, 0.5 mmol, 1.0 eq), tetrabutylammonium bromide (199 mg, 0.6 mmol, 1.2 eq), $K_2CO_3$ (1.4 g, 10 mmol) and N-methylpyrrolidone (NMP, 30 ml) into a 100 ml three-necked flask; stirring at room temperature for 2 hours; slowly instilling a NMP (5 ml) solution containing alkyl ester (485.4 mg, 2 mmol, 4.0 eq) into the reaction solution; heating the reaction solution up to 60° C. and keeping the reaction for 48 hours; cooling the reaction solution down to room temperature after the reaction is completed; extracting the reaction solution with ethyl acetate/water; washing organic phases with 3 wt % oxalic acid solution and water, respectively for one time; combining organic layers; drying the organic layers with anhydrous $MgSO_4$; removing the solvent by decompressing; recrystallizing the obtained product with ethyl acetate/n-hexane mixture solvent to obtain a 745 mg pale yellow solid with the yield of 92%. $^1$H NMR (400 MHz, $CDCl_3$) δ (ppm) 7.88 (d, J=8.0 Hz, 4H), 7.55 (d, J=8.0, 4H), 6.87 (d, J=1.2 Hz, 4H), 6.45 (s, 8H), 4.45 (s, 8H), 1.67 (m, 68H). MS (MALDI-TOF): m/z=1635.7, calcd for $C_{101}H_{104}O_{20}$ m/z=1636.6 ([M]+).

EXAMPLE 9

Figure 2:
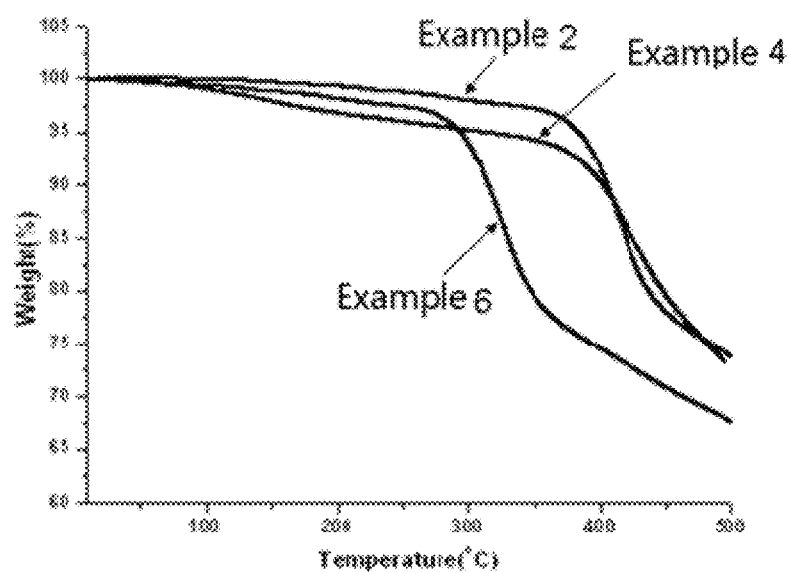
FIG. 2 shows a thermogravimetric graph.

Measured are the glass transition temperatures of spirofluorene derivative molecular glass prepared in examples 2, 4 and 6. The differential scanning thermal curves and thermal gravimetric analysis are shown respectively in FIGS. 1 and 2, and the results show that the glass transition temperatures of such molecular glass are all above 100° C., meanwhile such molecular glass has good thermal stability which meets the requirements of the photolithography process.

EXAMPLE 10

Figure 3:
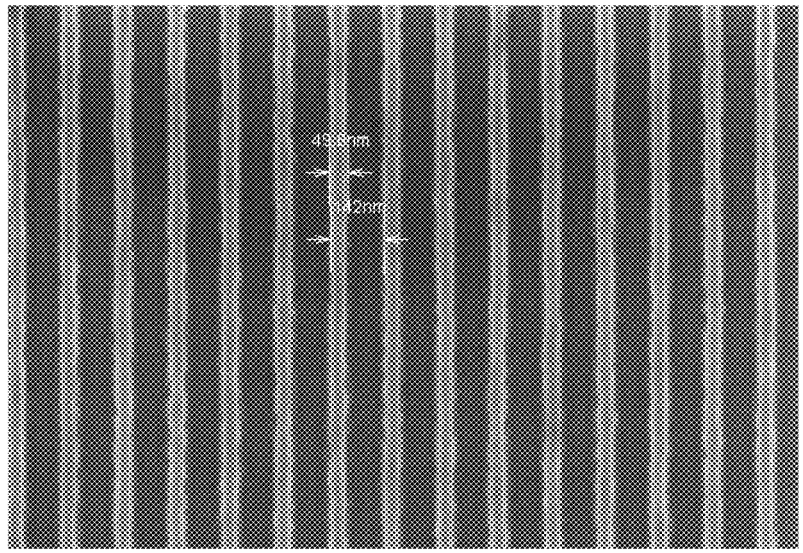
FIG. 3 shows an electron micrograph of fringes obtained with interference photolithography in example 10.

The positive photoresist formula and experiment on photolithography, comprising the steps of: dissolving the compound 2,7,2',7'-four-(3,4-di-t-butyl carbonate phenyl)-9,9'-spirofluorene of example 6 in propylene glycol monomethyl ether acetate (PGMEA) to obtain a solution with the mass concentration of 3%; adding and dissolving trifluoromethanesulfonic acid triphenylsulfonium salt with the mass concentration of 0.15% as a photo-acid-generating agent into the solution; filtering the solution with a micropore filter with the pore size of 0.22 μm to obtain spin-coating liquid; spin-coating the liquid onto a silicon substrate treated by acid and alkali, and obtaining a film with a uniform thickness. The prepared film is exposed in soft X-ray interference photolithography line station (BL08U1B) of Shanghai synchrotron radiation source, with the exposure period of 140 nm, to obtain very uniform photolithographic fringes, as shown in FIG. 3. The photolithographic fringe has 50 nm width with good resolution, contrast and low line edge roughness.

EXAMPLE 11

Figure 4:
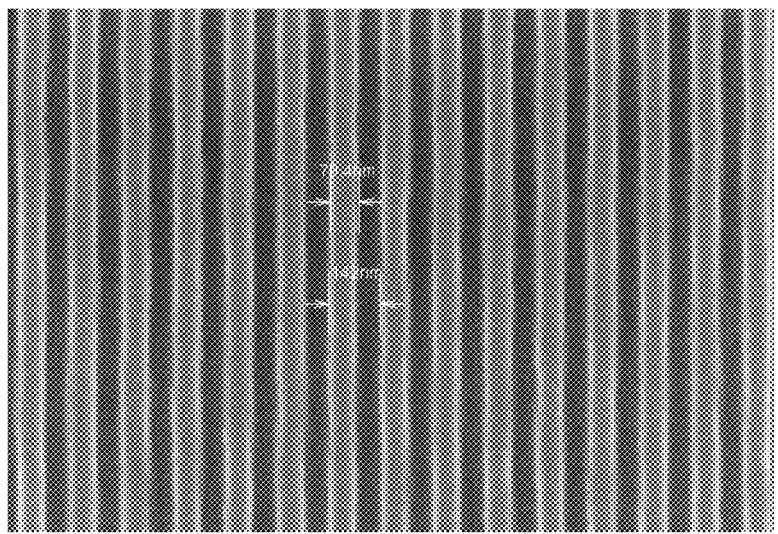
FIG. 4 shows an electron micrograph of fringes obtained with interference photolithography in example 11.

The design of a negative photoresist formula comprises steps of: dissolving compound 2,7,2',7'-four-(3,5-dihydroxyphenyl)-9,9'-spirofluorine of example 3 in ethyl lactate to obtain a solution with the mass concentration of 10%; adding 1,3,4,6-tetrakis(methoxymethyl)glycoluril with 1% mass concentration as a cross linking agent and triphenylsulfonium trifluoromethanesulfonate with 0.5% mass concentration as a photo-acid-generating agent into the solution; filtering the solution with a micropore filter with the pore size of 0.22 μm to obtain spin-coating liquid, spin-coating the liquid onto a silicon substrate treated by acid and alkali, and obtaining a film with uniform thickness. The prepared film is exposed in soft X-ray interference photolithography line station (BL08U1B) of Shanghai synchrotron radiation source, with the exposure period of 140 nm, to obtain very uniform photolithographic fringes, as shown in FIG. 4. The photolithographic fringe has about 70 nm width with good resolution, contrast and low line edge roughness.

Obviously, the above embodiments of the present invention are only the examples for illustrating clearly the present invention and should not be interpreted as any limitations to the present invention. Various variations or modifications can be made for one skilled in the art based on the above description. Here all of the embodiments could not be provided exhaustively. Obvious variations or modifications derived from the technical solution of the present invention will fall in the protection scope of the present invention.

The invention claimed is:

1. A spirofluorene derivative molecular glass, having the following molecular structure:

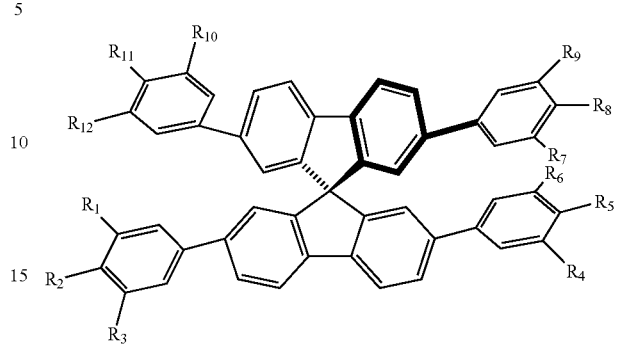

wherein:
  substituents $R_1$-$R_{12}$ are a hydrogen atom, a hydroxyl group, a methoxyl group or an acid sensitive substituent, respectively; substituents $R_1$-$R_{12}$ can be same or different, but the substituents of a same benzene ring cannot all be hydrogen atoms.

2. The spirofluorene derivative molecular glass of claim 1, wherein the acid-sensitive substituent is alkane carbonic ester with no more than 12 carbon atoms, and the structure thereof is:

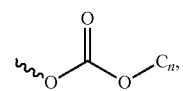

or alkane α-acetate substituent, and the structure thereof is:

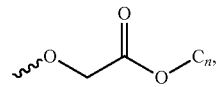

wherein $Cn=C_{1-12}$ alkyl, ~~~ represents a connecting bond.

3. The spirofluorene derivative molecular glass of claim 2, wherein the alkane carbonic ester with no more than 12 carbon atoms or alkane α-acetate substituent is a group with the following structure:

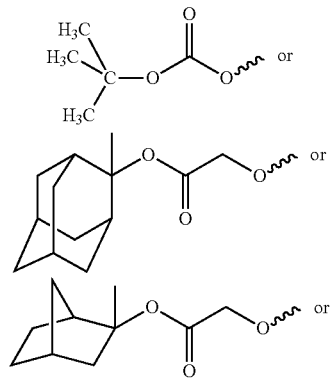

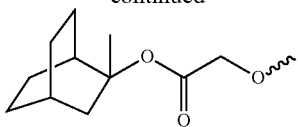

wherein, ~~~ represents a connecting bond.

4. A method for preparing the spirofluorene derivative molecular glass of claim 1, comprising the following steps of:
1) under the protection of an inert gas, mixing spirofluorene having tetrabromo substituents with phenyl boride having methoxy substituents with different numbers and at different sites by 1:4-8 molar ratio; adding palladium acetate as a catalyst with catalytic amount and a tetrahydrofuran solution; heating up to 50-70° C. and keeping reaction for 6-24 hours to obtain a spirofluorene derivative having different phenylmethoxy substituents;
2) under the protection of an inert gas, mixing the spirofluorene derivative obtained in step 1) with BBr₃ by 1:8-10 molar ratio; producing a deprotection reaction in a dichloromethane solvent at −50° C.-80° C. to obtain a spirofluorene derivative with phenolic hydroxyl groups at the periphery thereof;
3) under the protection of an inert gas, mixing the spirofluorene derivative obtained in step 2) and a compound containing an acid-sensitive substituent by 1:4-18 molar ratio; adding pyridine or potassium carbonate as a catalyst; producing a reaction at room temperature for 10-24 hours to obtain a spirofluorene derivative molecular glass.

5. The method for preparing spirofluorene derivative molecular glass of claim 4, wherein the phenyl boride having methoxy substituents with different numbers and at different sites is one or more selected from the group consisting of p-methoxyphenyl pinacol borane, m-methoxyphenyl pinacol borane, 3,4-dimethoxyphenyl pinacol borane, 3,5-dimethoxyphenyl pinacol borane and 3,4,5-trimethoxyphenyl pinacols borane.

6. The method for preparing spirofluorene derivative molecular glass of claim 4, wherein the compound containing an acid-sensitive substituent has the following structure:

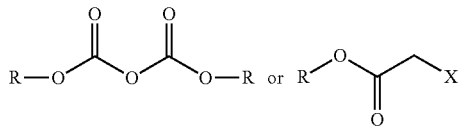

wherein, R represents an alkyl with no more than 12 carbon atoms; X=Cl, Br or I.

7. The method for preparing spirofluorene derivative molecular glass according to claim 6, wherein the compound containing an acid-sensitive substituent has the following structure:

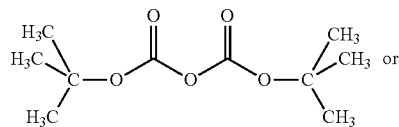

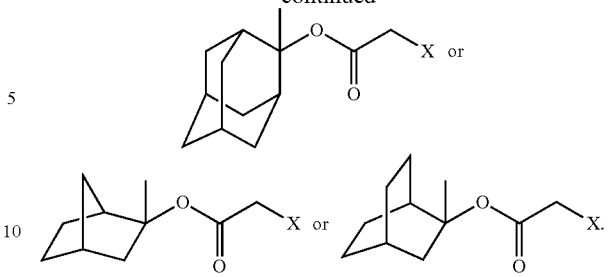

8. A negative photoresist, comprising a spirofluorene derivative molecular glass having a molecular structure I, a photo-acid-generating agent, a cross linking agent and a photoresist solvent,

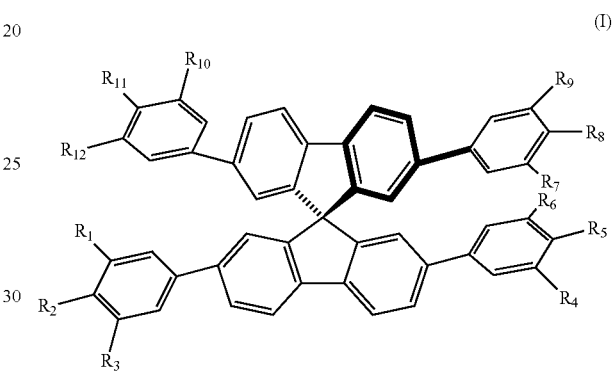

wherein substituents $R_1$-$R_{12}$ are a hydrogen atom, a hydroxyl group, a methoxy group or an acid sensitive substituent, respectively; substituents $R_1$-$R_{12}$ can be same or different, but the substituents of a same benzene ring cannot all be hydrogen atoms,
and wherein at least one substituent $R_1$-$R_{12}$ is a hydroxyl group.

9. The negative photoresist of claim 8, wherein at least four substituents $R_1$-$R_{12}$ are hydroxyl groups.

10. The negative photoresist of claim 9, wherein the photo-acid-generating agent is one or more selected from a group consisting of triphenylsulfonium trifluoromethanesulfonate, bis(4-tert-butylphenyl)iodonium p-toluenesulfonate and N-hydroxynaphthalimide triflate; the cross linking agent is one or two selected from a group consisting of 1,3,4,6-tetrakis(methoxymethyl)glycoluril and 2,4-hydroxymethyl-6-methyl-phenol; the photoresist solvent is one or more selected from a group consisting of propylene glycol monomethyl ether acetate, ethyl lactate, 2-methoxyethanol and cyclohexanone.

11. The negative photoresist of claim 8, wherein the content of the spirofluorene derivative molecular glass is 1 wt %-10 wt %, the content of the cross linking agent is 0.1 wt %-1 wt %, the content of photo-acid-generating agent is 0.01 wt %-1 wt % and the remainder is the photoresist solvent.

12. The negative photoresist of claim 11, wherein the photo-acid-generating agent is one or more selected from a group consisting of triphenylsulfonium trifluoromethanesulfonate, bis(4-tert-butylphenyl)iodonium p-toluenesulfonate and N-hydroxynaphthalimide triflate; the cross linking agent is one or two selected from a group consisting of 1,3,4,6-tetrakis(methoxymethyl)glycoluril and 2,4-hydroxymethyl-6-methyl-phenol; the photoresist solvent is one or more selected from a group consisting of propylene glycol monomethyl ether acetate, ethyl lactate, 2-methoxyethanol and cyclohexanone.

13. The negative photoresist of claim 8, wherein the photo-acid-generating agent is one or more selected from a group consisting of triphenylsulfonium trifluoromethanesulfonate, bis(4-tert-butylphenyl)iodonium p-toluenesulfonate and N-hydroxynaphthalimide triflate; the cross linking agent is one or two selected from a group consisting of 1,3,4,6-tetraki (methoxymethyl)glycoluril and 2,4-hydroxymethyl-6-methyl-phenol; the photoresist solvent is one or more selected from a group consisting of propylene glycol monomethyl ether acetate, ethyl lactate, 2-methoxyethanol and cyclohexanone.

14. A positive photoresist, comprising a spirofluorene derivative molecular glass having a molecular structure I, a photo-acid-generating agent and a photoresist solvent,

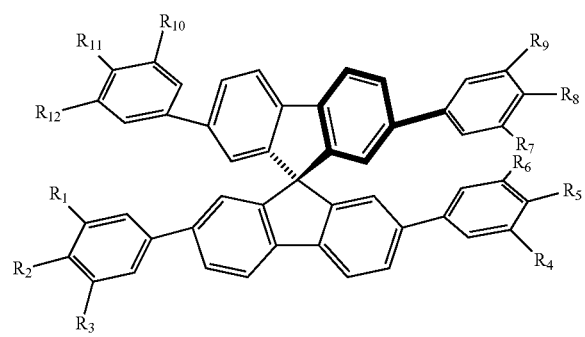
(I)

wherein substituents $R_1$-$R_{12}$ are a hydrogen atom, a hydroxyl group, a methoxyl group or an acid sensitive substituent, respectively; substituents $R_1$-$R_{12}$ can be same or different, but the substituents of a same benzene ring cannot all be hydrogen atoms, and wherein at least one substituent $R_1$-$R_{12}$ is an acid-sensitive substituent.

15. The positive photoresist according to claim 14, wherein at least four substituents $R_1$-$R_{12}$ are acid-sensitive substituents.

16. The positive photoresist of claim 15, wherein the photo-acid-generating agent is one or more selected from a group consisting of triphenylsulfonium trifluoromethanesulfonate, bis(4-tert-butylphenyl)iodonium p-toluenesulfonate and N-hydroxynaphthalimide triflate; the photoresist solvent is one or more selected from a group consisting of propylene glycol monomethyl ether acetate, ethyl lactate, 2-methoxyethanol and cyclohexanone.

17. The positive photoresist according to claim 14, wherein the content of the spirofluorene derivative molecular glass is 1 wt %-10 wt %, the content of the photo-acid-generating agent is 0.01 wt %-1 wt % and the remainder is the photoresist solvent.

18. The positive photoresist of claim 17, wherein the photo-acid-generating agent is one or more selected from a group consisting of triphenylsulfonium trifluoromethanesulfonate, bis(4-tert-butylphenyl)iodonium p-toluenesulfonate and N-hydroxynaphthalimide triflate; the photoresist solvent is one or more selected from a group consisting of propylene glycol monomethyl ether acetate, ethyl lactate, 2-methoxyethanol and cyclohexanone.

19. The positive photoresist of claim 14, wherein the photo-acid-generating agent is one or more selected from a group consisting of triphenylsulfonium trifluoromethanesulfonate, bis(4-tert-butylphenyl)iodonium p-toluenesulfonate and N-hydroxynaphthalimide triflate; the photoresist solvent is one or more selected from a group consisting of propylene glycol monomethyl ether acetate, ethyl lactate, 2-methoxyethanol and cyclohexanone.

* * * * *